United States Patent [19]
North, Jr.

[11] Patent Number: 5,915,925
[45] Date of Patent: Jun. 29, 1999

[54] PULSELESS LIQUID SUPPLY SYSTEM FOR FLOW CYTOMETRY

[76] Inventor: Howard L. North, Jr., 100 Via Santa Maria, Los Gatos, Calif. 95032

[21] Appl. No.: 08/779,505

[22] Filed: Jan. 7, 1997

[51] Int. Cl.⁶ .................................................. F04B 49/06
[52] U.S. Cl. ........................... 417/36; 417/32; 417/44.9; 73/149; 73/290 B
[58] Field of Search .................. 417/32, 36, 37, 417/44.9; 73/149, 290 B, 168

[56] References Cited

U.S. PATENT DOCUMENTS

| | | | |
|---|---|---|---|
| 3,349,785 | 10/1967 | Duffy | 137/30 |
| 3,738,776 | 6/1973 | Debare | 417/38 |
| 3,826,364 | 7/1974 | Bonner et al. | 209/3 |
| 3,937,596 | 2/1976 | Braidwood | 417/36 |
| 3,958,898 | 5/1976 | Abrahams et al. | 417/36 |
| 4,278,403 | 7/1981 | Shaefer | 417/38 |
| 4,738,595 | 4/1988 | Gaiser | 417/36 |
| 5,213,477 | 5/1993 | Watanabe et al. | 417/20 |
| 5,253,982 | 10/1993 | Niemiec et al. | 417/38 |
| 5,315,867 | 5/1994 | Hartel et al. | 73/149 |
| 5,385,069 | 1/1995 | Johnson, Jr. | 73/571 |
| 5,425,624 | 6/1995 | Williams | 417/36 |
| 5,777,221 | 7/1998 | Murthy et al. | 73/149 |

*Primary Examiner*—Charles G. Freay
*Assistant Examiner*—Ehud Gartenberg

[57] ABSTRACT

A liquid supply system for flow cytometry apparatus including a diaphragm pump, a novel liquid accumulator providing exceptionally high volume compliance, and a control of accumulator volume within narrow limits by continuous control of power to the pump motor. The accumulator achieves high volume compliance by arranging the kinematics of a main spring loading the accumulator to have a negative spring rate equal to the sum of all other positive spring rates produces by a second spring used to adjust the accumulator pressure, by the diaphragm, and by a flexure pivot support for a sensor lever. This sensor lever moves with the accumulator diaphragm to actuate an optical sensor producing an electric signal indicative of small changes in liquid volume in the accumulator. This signal in turn continuously modulates the power to the motor driving the pump so as to maintain the accumulator liquid volume close to a datum value even during a portion of the pump delivery cycle. This close control of liquid volume in a high compliance accumulator provides substantially pulse-free constant pressure liquid delivery from a pulsatile pump. The second spring may be adjusted to modify this constant pressure without disturbing the balance between positive and negative spring rates. Adjustment may be manual or automatic in response to a variable such as fluid temperature whereby liquid pressure is automatically increased with lower liquid temperatures to maintain liquid flow substantially constant through a flow cytometry apparatus used for particle analysis or particle sorting or the like.

2 Claims, 4 Drawing Sheets

PULSELESS LIQUID SUPPLY SYSTEM FOR FLOW CYTOMETRY

BACKGROUND OF THE INVENTION a) Field of the Invention

The invention relates to a system for delivering pressurized liquid to a flow cytometer, and in particular to a system having an improved liquid accumulator/pump control means for providing continuous modulation of power to a liquid pump drive means.

b) Description of the Related Art

Flow cytometry apparatus has commonly used a liquid suspension of particles ensheathed by a particle-free liquid wherein this coaxial flow passed through an analysis region and thence often to a particle sorting means. Such coaxial flow systems are shown in an article by P. J. Crossland-Taylor, Nature 171,37 (1953) and in U.S. Pat. No. 3,826,364, which are hereby referred to and incorporated herein. Sheath liquid is usually a phosphate buffered saline solution and is usually supplied to the analysis region from a closed reservoir pressurized by air from an air pressure regulator connected to a source of air at a higher pressure (note items 16, 26 and 22 of U.S. Pat. No. 3,826,364). Since particle analyzers and particle sorters often depend on consistent liquid flow velocities through the analysis region, this air pressurized sheath supply system has the following shortcomings:

1) As the sheath supply empties during operation of the flow cytometer, the loss of head causes a decrease in liquid flow;
2) Changes in sheath liquid temperature cause changes in sheath liquid flow rate due to changes in liquid viscosity. Changes in liquid temperature can result from a) changing ambient air temperature at the sheath reservoir, b) reservoir replenishment with sheath liquid at a different temperature such as from a remote storage area and/or steam sterilization of sheath liquid;
3) Replenishment of sheath liquid is inconvenient, requiring stopping operation of the flow cytometer, de-pressurizing the reservoir, opening and refilling the reservoir, re-pressurizing the reservoir and restarting the flow cytometer;
4) The pressurized reservoir has often been a stainless steel ASME pressure vessel which is both expensive and unsuitable for visual observation of liquid level in the reservoir;
5) Air dissolves in the sheath liquid in time and can later be released as bubbles as the liquid loses pressure while flowing through filters, valves, and conduits to the analysis and sorting regions. Bubbles in these regions often prevent proper analysis or sorting functions; and
6) When a pressurized air supply is not available at a flow cytometer installation, then a separate air compressor, motor, reservoir, and controls must be provided.

Attempts to use gear or centrifugal pumps to pressurize sheath liquid, usually a phosphate buffered saline, have not produced practical designs. Neither pump is inherently self-priming so initial start up or restart after running out of liquid requires the operator to perform special procedures such as bleeding air from the system. If either pump is kept running when liquid flow through the cytometer stops, then the pump will tend to overheat and be damaged. Solutions such as an overflow/over pressure line for returning pressurized liquid back to the supply reservoir or stopping the pump add cost and complexity. Also gear and centrifugal pumps suitable for long life operating with corrosive saline are expensive.

Many of these shortcomings of gear or centrifugal pumps are avoided by diaphragm pumps, particularly those with polymer housings and with elastomer diaphragms and check valves. However, diaphragm pumps require a liquid accumulator to supply pressurized liquid during the refilling stroke of the pump. Common accumulators employ a piston loaded by a spring or a bladder loaded by compressed gas or combinations thereof (as is shown in U.S. Pat. No. 4,278,403. This patent shows an accumulator 35 which operates a pump P via a switch 43 in an on/off mode from a pressure movable partition element, piston 36. This on/off mode of pump control with its dead band between On and Off conditions results in significant changes in pressure in accumulator 35. In addition the friction from seals for piston 36 and stem 41 produce inaccuracies in the sensing of pressure in accumulator 35. Also these seals are subject to wear and leakage which limit the durability of accumulator 35.

OBJECTS AND ADVANTAGES

Accordingly, several objects and advantages of my invention are:

a) to provide essentially pulse-free constant pressure sheath liquid to a flow cytometer unaffected by liquid level changes in the supply reservoir;
b) to employ an unpressurized supply reservoir which is easy to refill, is simple and low cost, may be raised and lowered without affecting the sheath supply pressure, does not introduce air into the sheath liquid, does not require a separate air supply and valves, may be sized large to reduce replenishment frequency, may be transparent for visual observation of liquid level, and may be replenished without stopping operation of the flow cytometer;
c) to provide for manual or automatic adjustment of the sheath liquid pressure as required to compensate for variations in sheath liquid temperature and thereby maintain sheath flow rate substantially constant and thus maintain critical flow cytometer timing such as:
Particle transit time from laser beam to drop break-off for drop-in-air sorters,
Particle transit time from laser beam to catcher tube for a catcher tube sorter,
Particle transit time between laser beams in a multiple laser analyzer or sorter;
d) to provide a novel liquid accumulator which can accept the liquid volume delivered by one stroke of a diaphragm pump with negligible change (less than 0.1%) in liquid pressure; and
e) to provide a self-priming pump in a sheath liquid supply system where sheath liquid contacts only non-metal parts thus avoiding metal corrosion and contamination of the sheath liquid.

Other objects and advantages are to provide apparatus and method for delivering pressurized sheath liquid to a flow cytometer which is small, simple, low cost, reliable, durable, quiet, accurate, essentially pulse-free, and which operates with low electrical power.

SUMMARY OF THE INVENTION

Briefly, the present invention is directed to a pulse free, constant pressure liquid supply system which may be adapted for connection to a flow cytometer. Preferred embodiments of the invention provide for manual or automatic adjustment of the liquid pressure to compensate for variations in liquid supply temperature and thus maintain liquid flow constant through the flow cytometer. This invention avoids many of the problems, inconveniences, and cost associated with earlier liquid supply systems by use of a novel liquid accumulator design and an electric motor driven reciprocating diaphragm pump controlled by a simple electronic control responsive to the liquid volume in the accumulator.

BRIEF DESCRIPTION OF THE DRAWINGS

The invention may be understood, and further advantages and uses are more readily apparent, when considered in view of the following detailed description of the exemplary embodiments, taken with the accompanying drawings, in which.

DESCRIPTION OF THE PREFERRED EMBODIMENTS

Figure 1:
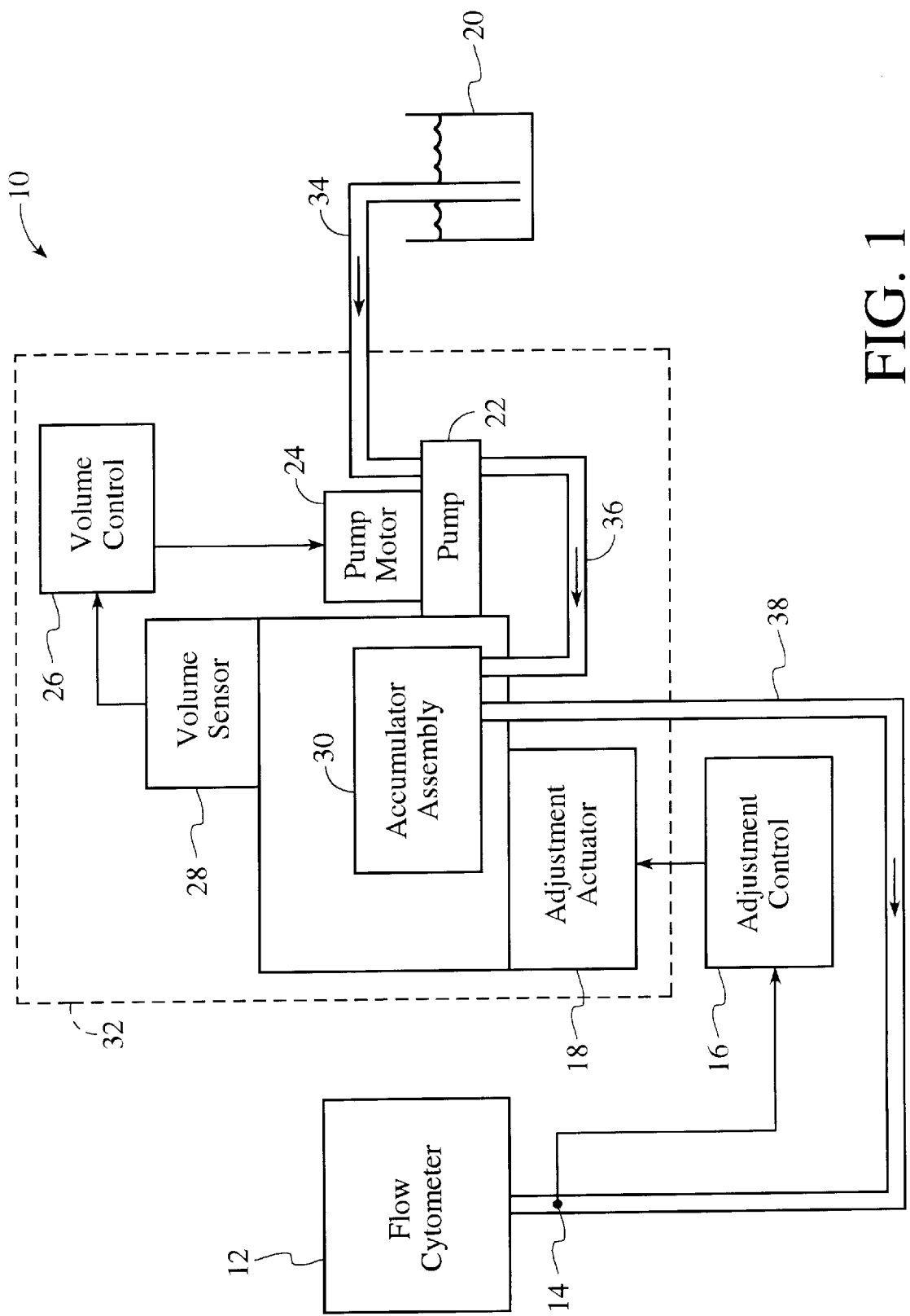
FIG. 1 is a simplified schematic diagram of the liquid supply system.

Referring now to the drawings and to FIG. 1 in particular, there is shown a simplified schematic diagram of liquid supply system 10 supplying flow cytometer 12 with a constant liquid flow, all constructed accordingly to the teachings of the invention. Liquid supply system 10 includes reservoir 20 connected via conduit 34 to pump 22, thence via conduit 36 to accumulator assembly 30, thence via conduit 38 to the inlet of flow cytometer 12. Accumulator assembly 30 is part of liquid supply control means 32 for supplying a constant flow of liquid to flow cytometer 12 which includes pump 22, pump motor 24, volume sensor 28, volume control 26, and adjustment actuator 18. Liquid supply system 10 further includes adjustment control 16 connected to liquid temperature sensor 14 and adjustment actuator 18.

Figure 2:
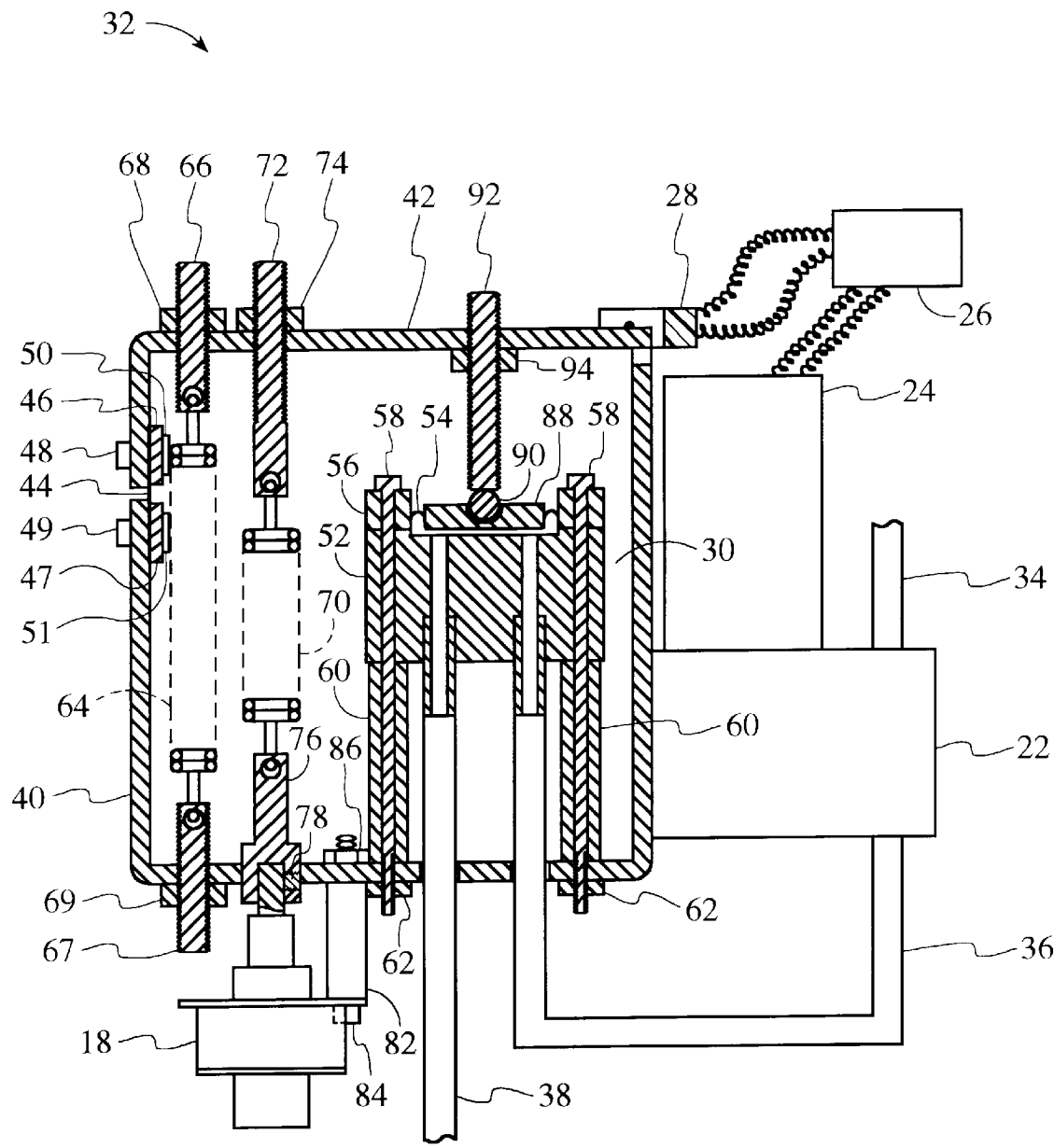
FIG. 2 is a cross-sectional view of the liquid supply assembly taken along the line 2—2 of FIG. 3.

Referring now to FIG. 2 there is shown a cross sectional view (taken along the line 2—2 of FIG. 3) through the middle of liquid supply assembly 32 which shows accumulator assembly 30 including diaphragm 54 clamped between diaphragm retainer 56 and accumulator body 52 by screws 58, 4 spacers 60, main support 40 and 4 nuts 62. Diaphragm 54 is of the constant area rolling diaphragm type such as for example are manufactured by Bellofram Corporation. Diaphragm 54 is connected via piston 88, ball 90, diaphragm screw 92, and nut 94 to sensor lever 42. Sensor lever 42 is pivotably supported by flexure pivot 44 clamped to sensor lever 42 by flexure retainer 46, two screws 48, and two nuts 50 and is clamped to main support 40 by flexure retainer 47, two screws 49 and two nuts 51. A main spring 64 is attached to sensor lever 42 by main spring support screw 66 and nut 68 and is attached to main support 40 by main spring support screw 67 and nut 69. Main spring 64 is a helical extension spring with a hook at each end for insertion in a hole in spring support screws 66 and 67. An adjustment spring 70 is attached to sensor lever 42 by adjustment spring support screw 72 and nut 74 and to adjustment actuator 18 by coupling 76 and set screw 78. Adjustment spring 70 is a helical extension spring with a hook at each end for insertion in a hole in spring support screw 72 and in coupling 76. Adjustment actuator 18 is fastened to main support 40 by two spacers 82, two screws 84 and two nuts 86. The adjustment actuator 18 may be for instance, a stepper motor driven linear actuator such as manufactured by Haydon Switch and Instrument and sold under Model No. 26541 which has 0.001 inch motion per electrical step. Pump 22 and pump motor 24 may be an integrated assembly such as is manufactured by KNF Neuberger under Model No. NF30KVDC or NF1.30KVDC which are rated for continuous pumping at pressures up to 15 and 85 psi respectively. Pump motor 24 and volume sensor 28 are connected electrically to volume control 26. Pump 22 with pump motor 24 may be mounted on main support 40 or elsewhere. Liquid supply assembly 32 is preferably oriented so air is naturally purged from accumulator assembly 30 and pump 22 when liquid flows through these components during start up.

Figure 3:
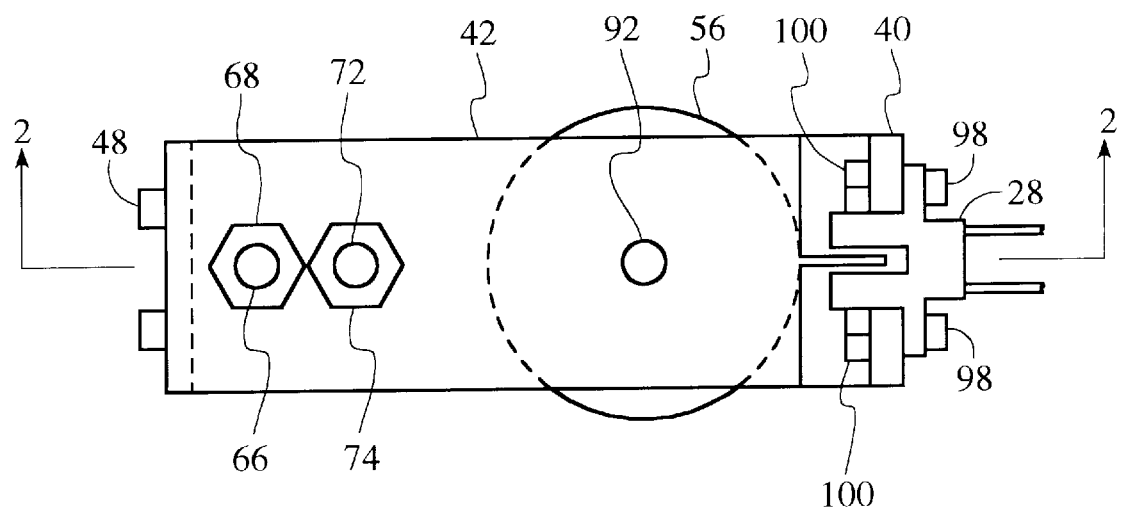
FIG. 3 is a plan view of the volume sensor.

Referring now to FIG. 3 there is shown a plan view of sensor lever 42 and volume sensor 28 which is fastened to main support 40 by screws 98 and two nuts 100. Volume sensor 28 comprises an infrared light emitting diode facing an NPN silicon phototransistor encased in a black thermoplastic housing such as for example manufactured and sold by Honeywell under the Model No. HOAO890-T51. The reduced width end of sensor lever 42 is located within a slot between the light emitting diode and the phototransistor.

Figure 4:
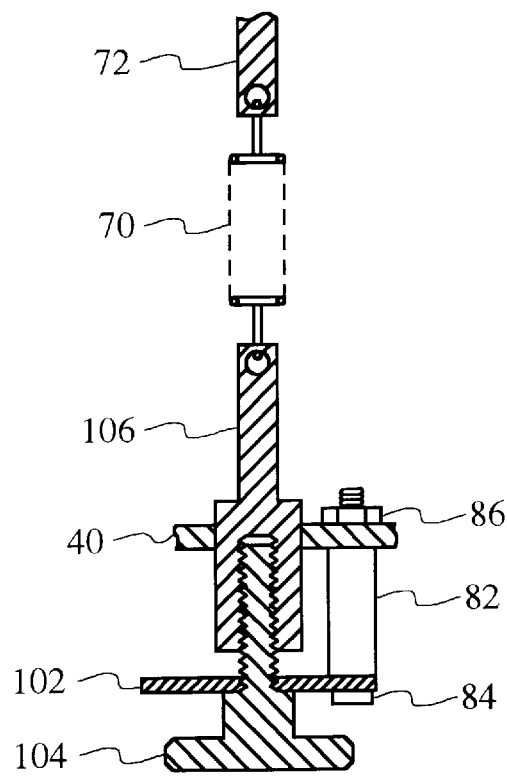
FIG. 4 is a cross sectional view of the manual pressure adjustment.

Referring now to FIG. 4, there is shown a cross-sectional view of the manual pressure adjustment where the adjustment actuator 18, coupling 76, and set screw 78 have been replaced by support plate 102, and manual adjustment 104 which is threadably engaged with manual adjustment coupling 106 which is slidably engaged with main support 40 in a non-round hole to prevent rotation of manual adjustment coupling 106.

Figure 5:
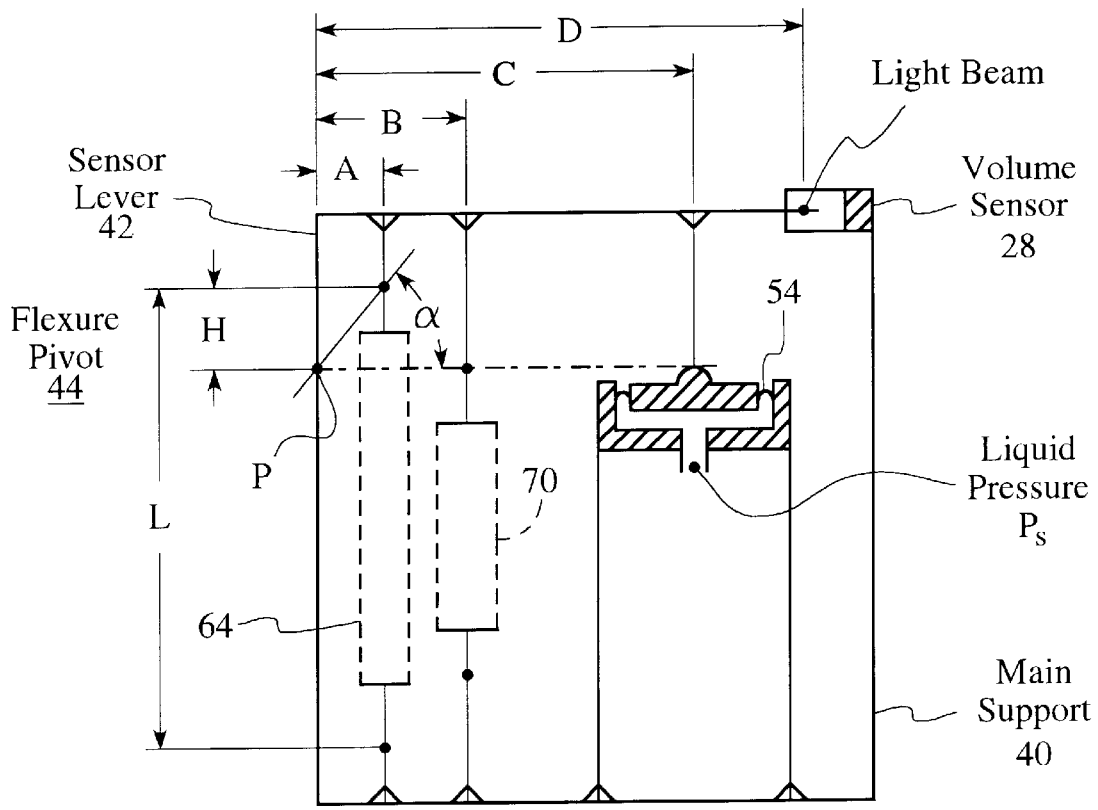
FIG. 5 is a diagram of the kinematic features of the invention.

Referring now to FIG. 5 there is shown a diagram of the essential kinematic features of the invention provided to facilitate explanation of the design of an accumulator having substantially infinite volume compliance. Volume compliance is defined as a small change in accumulator volume divided by the resulting change in accumulator pressure. A,B,C,&D are dimensions from the flexure pivot 44 pivot point P to the centerlines for the forces from main spring 64, adjustment spring 70, diaphragm 54, and the light beam of Volume sensor 28 respectively. H is the height above pivot point P of the contact of main spring 64 with main spring support screw 66. a is the angle defined by tan a=H/A. L is the installed length of main spring 64 between contacts with main spring support screws 66 and 67. The following terms are defined here:

$K_M$ is the spring rate of main spring 64 in lbs./inch $K_A$ is the spring rate of adjustment spring 70 in lbs./inch $K_D$ is the spring rate of diaphragm 54 in lbs./inch $T_P$ is the torsional spring rate of flexure pivot 44 as installed, in inch-lbs./radian, defined as the rate of change in moment about pivot P per radian change in angle a due to motion of sensor lever 42 about pivot P $A_D$ is the effective area of diaphragm 54 exposed to liquid pressure in square inches $P_S$ is the liquid pressure in the accumulator acting on the diaphragm in psi.

$F_M$ is the tension force of main spring 64 in lbs.

$F_A$ is the tension force of adjustment spring 70 in lbs.

$$\text{Accumulator Compliance (cubic inch/psi.)} = \frac{A_D 2}{K_D + K_A B^2/C^2 + T_P/C^2 + K_M A^2/C^2 - F_M\left(\frac{L-H}{L}\right)\frac{H}{C^2}}$$

Figure 6:
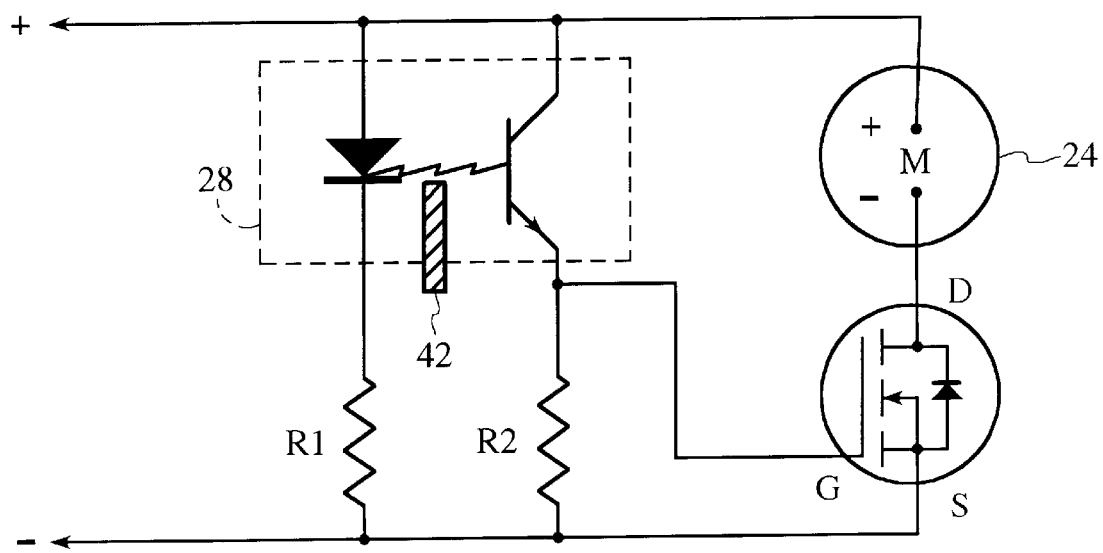
FIG. 6 is an electrical diagram of the volume sensor, volume control, and pump motor.

Referring now to FIG. 6 there is shown a typical volume control 26 used with volume sensor 28 and pump motor 24. Typical components are IRF520 N channel MOSFET, $R_1$=560 ohm, and $R_2$=470,000 ohm.

Referring again now to FIG. 1, in operation there will be liquid flow from the supply reservoir 20 through conduit 34 to pump 22 and then through conduit 36 to accumulator assembly 30 and then through conduit 38 to flow cytometer 12. Pump 22 is driven by pump motor 24 which is controlled by volume control 26 which is responsive to volume sensor 28. Referring now to FIG. 2, there is shown that as less liquid is contained in accumulator assembly 30 diaphragm 54 and piston 88 move towards accumulator body 52. In turn ball 90, diaphragm screw 92, nut 94, and sensor lever 42 also move towards accumulator body 52. Sensor lever 42 then moves to permit more light from the light emitting diode to reach the phototransistor in volume sensor 28 which increases the phototransistor conductivity. As shown on and referring now to FIG. 6, this increases the voltage between the gate G and the source S of the MOSFET which increases the current through pump motor 24 driving pump 22. Pump 22 then increases its discharge of liquid into accumulator assembly 30 which causes diaphragm 54, piston 88, ball 90, diaphragm screw 92, nut 94, and sensor lever 42 to move away from accumulator body 52. This motion of sensor lever 42 reduces the light from the light emitting diode reaching the phototransistor in volume sensor 28 which reduces its conductivity. This decreases the voltage between the gate and the source of the MOSFET which reduces the current (and the torque) through the pump motor 24 driving pump 22. Pump 22 then slows down or stops delivering liquid to accumulator assembly 70. In this manner, balance is obtained in this closed-loop control system. This balance is obtained both statically and dynamically throughout the delivery stroke of pump 22 from bottom dead center to near top dead center. However, near the top dead center the control loop tends to become unstable and a small fraction of the stroke volume of pump 22 is delivered to accumulator assembly 30 whether needed or not needed. This fraction is typically less than 1% of the stroke volume of pump 22. After passing top dead center, pump 22 refills from reservoir 20 and returns to bottom dead center rapidly for continued control of liquid volume within accumulator assembly 30.

It is clear that accumulator assembly 30 will have small but significant volume changes during each delivery cycle of pump 22. The liquid supply assembly 32 is provided with a novel kinematic design so that supply pressure $P_S$ within accumulator assembly 30 is essentially unaffected by these small liquid volume changes whereby $P_S$ is fixed within less than +or–0.1% fluctuation during continued operation of pump 22. This accumulator function is produced by arranging the main spring 64 kinematically to produce a negative spring rate at diaphragm 54 which numerically equals the positive spring rate at diaphragm 54 produced by the sum of the spring rates of diaphragm 54, adjustment spring 70 and flexure pivot 44. Referring now to FIG. 5 the negative spring rate effect of main spring 64 is produced by making H large enough in relation to the other parameters that as sensor lever 42 moves to increase angle a, the fractional decrease in moment arm from main spring force to pivot P is greater than the fractional increase in force from the main spring due to its greater extension. The net effective spring rate, $K_e$, at the diaphragm 54 centerline is given by:

$$K_e = K_D + K_A B^2/C^2 + T_P/C^2 + K_M A^2/C^2 - F_M[(L-H)/L]H/C^2 \text{ lb./in.} \qquad \text{Eq. 1}$$

where $$T_P = Ewt^3/12h \text{ in. lb./radian} \qquad \text{Eq. 2}$$

where for pivot support 44:

E=Young's modulus of elasticity-psi w=width-inches t=thickness-inches h=height-inches The volume compliance, $C_{volume}$, of accumulator assembly 30 is:

$$C_{volume} = A_D^2/K_e \text{ in.}^3/\text{psi.} \qquad \text{Eq. 3}$$

Infinite compliance for small changes in liquid volume is obtained when $K_e$=0. By setting $K_e$=0 in Eq. 1 and solving for H we obtain:

$$H = \frac{L \pm \sqrt{L^2 - 4m}}{2} \qquad \text{Eq. 4}$$

$$\text{where } m = L(K_D C^2 + K_A B^2 + T_P + K_M A^2)/F_M \qquad \text{Eq. 5}$$

Eq. 4 provides two solutions for H. Each positive, real solution is valid and may be used. Where two valid solutions exist the smaller H is preferred since it results in a more compact liquid supply assembly 32.

The supply liquid pressure, $P_S$, in accumulator assembly 30 is:

$$P_S = \frac{F_M(A/C) + F_A(B/C) + F_D + (T_P \times \text{change in } a)/C}{A_D} \text{psi} \qquad \text{Eq. 6}$$

Normally diaphragm 54 and flexure pivot 44 are undeflected from their relaxed positions and thus $F_D$ and change in a are nearly zero and may be neglected. Eq. 6 becomes:

$$P_S = \frac{F_M(A/C) + F_A(B/C)}{A_D} \text{psi} \qquad \text{Eq. 7}$$

$F_M$ is set to give the desired minimum value of $P_S$ when $F_A$ is zero. H is calculated from this value of $F_M$ using Eqs. 4 and 5. Then $F_A$ is calculated to give the maximum value of $P_S$.

$F_A$ is adjusted by varying the extension of adjustment spring 70 by linear motion produced by adjustment actuator 18 which moves one end of adjustment spring 70 through coupling 76. The other end of adjustment spring 70 is supported at a location opposite pivot P so that negligible changes in moment arm B occur with small changes in angle a. Thus there is no negative spring rate effect present with adjustment spring 70 which would cause $K_e$ to depart significantly from zero as $F_A$ is varied from minimum to maximum. The spring rate of adjustment spring 70 is chosen so the desired adjustment range of $P_S$ can be obtained with the available linear motion of adjustment actuator 18. For the preferred adjustment actuator 18 the available motion is about 0.500 inch with 0.001 inch per step of the stepping motor. For an adjustment range of 0–50% of $P_S$ each step therefore produces about 0.1% change in $P_S$. This provides fine control of $P_S$ setting.

When used with flow cytometer 12 the liquid supply system 10 is usually operated so as to increase Ps as liquid temperature entering the flow cytometer 12 decreases to compensate for the effects of increased liquid viscosity and thus maintain constant both liquid flow and velocity through flow cytometer 12. Constant liquid velocity allows for fixed settings for delay time in drop-in-air and catcher tube sorters as well as the transit time for cells passing between laser beams in a cell analyzer. Liquid temperature sensor 14 provides a signal to adjustment control 16 which then sends the appropriate number of electrical step signals to adjustment actuator 18 or drive it from a home or fixed starting position to the desired compensated operating position and thus apply the required extension to adjustment spring 70 to obtain the required supply pressure $P_S$. Adjustment control 16 may use an EPROM or other suitable memory device to accomplish the function of a look-up table of stepper motor steps versus fluid temperature. The adjustment control 16 has conventional electronics suitable for driving the stepper motor of the adjustment actuator 18. The adjustment control 16 may be implemented in various ways by those skilled in the art and is therefore not described in more detail here.

While the adjustment control 16 is shown as responsive to liquid temperature it is obvious that it could be responsive to any suitable operating parameter of flow cytometer 12 which can be sensed to provide either a closed loop control of that parameter or a programmed bias of $P_S$ produced in response to that parameter. Such parameters may be, for example, liquid flow as sensed by the transit time for a particle to pass through two laser beams or particle velocity as sensed by the time duration of a signal produced by a particle passing through the analysis region. A liquid flow parameter may also be sensed by the pressure drop across an orifice through which the liquid flows When such programmed or automatic control of $P_S$ is not required, $P_S$ may be adjusted by the apparatus shown in FIG. 4. The manual adjustment 104 is supported by support plate 102 and is threadably engaged with manual adjustment coupling 106 which is prevented from rotating by being slidably engaged in a non-circular hole in main support 40. As manual adjustment 104 is rotated, manual adjustment coupling 106 moves linearly to change the extension of adjustment spring 70. This changes its force, $F_A$, which in turn changes $P_S$ as set forth in Eq. 7. With a 32 thread per inch thread and a 50% change in $P_S$ with a 0.500 inch motion of manual adjustment coupling, there is about a 3% change in $P_S$ for each revolution of manual adjustment 104.

In conclusion, it can be readily understood that liquid supply system 10, constructed according to the teachings of the invention, provides a simple, compact, and economical apparatus for providing pulse-free, pressurized liquid having no additional dissolved air at a pressure which is independent of liquid level in the supply reservoir, wherein this pressure may be adjusted manually or automatically to compensate for liquid parameter changes, such as for example changes in liquid temperature to provide for constant liquid flow and constant velocity of particles passing through a flow cytometer analysis and/or sorting region(s).

While my above description contains many specifications, these should not be construed as limitations on the scope of the invention, but rather as an example of one preferred embodiment of the invention. Many other variations are possible without departing from the teachings of the invention, of which a few alternatives will now be described:

The diaphragm pump 22 could be replaced by a peristaltic tubing pump or any other pump with suitable characteristics. The volume sensor 28 could be replaced with any non-contact proximity sensor such as for instance Hall-effect or capacitive devices. The accumulator 30 could use an unconvoluted or flat diaphragm. The adjustment actuator 18 could be replaced by any suitable electromechanical devices such as for instance a rotary stepper motor driving a pinion gear coupled to a gear rack. It is also felt that adjustment actuator 18, liquid temperature sensor 14, and adjustment control 16 could be replaced by a non-electric means for adjustment of liquid pressure such as for instance a liquid thermal expansion apparatus. A sealed stainless steel bellows containing a liquid possessing a high thermal volume expansion characteristic could be placed in and exposed to the liquid passing through the accumulator body. One end of the bellows would be disposed in contact with the accumulator body. The other end of the bellows would be disposed so as to contact a compression spring interposed between the bellows and the accumulator diaphragm. In operation, as liquid temperature increases the liquid in the bellows expands, the bellows extends, the spring is further compressed, and the increased force on the diaphragm maintains constant regulated fluid pressure. Flexure pivot 44 may be replaced with any suitable low friction bearing such as a ball bearing. A KNF Neuberger NF 30 KVDC which is rated for 15 psig was selected for the pump 22 and pump motor 24 combination in the preferred embodiment. For higher pressures a KNF Neuberger NF 1.30 KVDC which is rated at 85 psig continuous operation may be substituted. Both pumps are manufactured by KNF Neuberger, Inc. of Trenton, N.J. Higher regulated liquid pressures may be obtained by use of a smaller area diaphragm in accumulator assembly 30 without increasing the size of the liquid supply assembly 32.

I claim:

1. An apparatus for providing a consistent liquid pressure output by continuously modulating power to a pump drive means, comprising:

a) an accumulator means having a diaphragm means for sensing the liquid volume in said accumulator means and assuming a position in response thereto;

b) sensing means for sensing the position of said diaphragm means responsive to said liquid volume in said accumulator means; and c) control means, responsive to said sensing means, for modulating power input to said pump drive means, providing increased power to said pump drive means when said liquid volume decreases and decreased power to said pump drive means when said volume level increases, wherein said sensing means comprises a light emitting diode (LED) and a photoreceptor that senses the position of said diaphragm.

2. The accumulator means of claim 1 wherein the accumulator is adapted for connection to a flow cytometer and wherein said accumulator means is temperature compensated by disposing a temperature compensating means in communication with said diaphragm means to maintain a temperature biased regulated pressure output from said accumulator means to said flow cytometer.

* * * * *